United States Patent
Hu et al.

(10) Patent No.: US 11,109,901 B2
(45) Date of Patent: Sep. 7, 2021

(54) QUICK RELEASE STERNUM CLOSING FIXATOR

(71) Applicant: Changzhou Waston Medical Appliance CO., LTD, Changzhou (CN)

(72) Inventors: Renmin Hu, Changzhou (CN); Jiaping Yang, Changzhou (CN); Fei Ma, Changzhou (CN); Dong Wei, Changzhou (CN)

(73) Assignee: CHANGZHOU WASTON MEDICAL APPLIANCE CO., LTD, Jiangsu (CN)

(*) Notice: Subject to any disclaimer, the term of this patent is extended or adjusted under 35 U.S.C. 154(b) by 185 days.

(21) Appl. No.: 16/538,343

(22) Filed: Aug. 12, 2019

(65) Prior Publication Data
US 2020/0337750 A1    Oct. 29, 2020

(30) Foreign Application Priority Data

Apr. 23, 2019    (CN) .......................... 201910329875.9

(51) Int. Cl.
| *A61B 17/80* | (2006.01) |
| *A61B 17/82* | (2006.01) |
| *A61B 17/68* | (2006.01) |

(52) U.S. Cl.
CPC ...... *A61B 17/8076* (2013.01); *A61B 17/8004* (2013.01); *A61B 17/8023* (2013.01); *A61B 17/823* (2013.01); *A61B 2017/681* (2013.01)

(58) Field of Classification Search
CPC .............. A61B 17/8076; A61B 17/823; A61B 17/8009
See application file for complete search history.

(56) References Cited

U.S. PATENT DOCUMENTS

| 8,758,417 | B2* | 6/2014 | Anderson | A61B 17/8076 606/324 |
| 2003/0083694 | A1* | 5/2003 | Miller, III | A61B 17/8009 606/216 |
| 2005/0277939 | A1* | 12/2005 | Miller, III | A61B 17/823 606/71 |
| 2006/0167458 | A1* | 7/2006 | Gabele | A61B 17/8076 606/916 |

(Continued)

FOREIGN PATENT DOCUMENTS

| CN | 102335035 A | 2/2012 |
| CN | 103211632 A | 7/2013 |

(Continued)

*Primary Examiner* — Olivia C Chang
(74) *Attorney, Agent, or Firm* — Novick, Kim & Lee, PLLC; Allen Xue

(57) ABSTRACT

A quick release sternum closing fixator has a locking roller, and a male fixing piece and a female fixing piece that can be plugged together. The male fixing piece has an elastic plug and the first claw hook plate. The elastic plug has the first serration on both sides and a tightening groove in the middle, thus forming two elastic claws. A tensioning device forces the two elastic claws to move against each other is provided between the said locking roller and the two elastic claws. After the locking roller rotates, when the elastic claws on the male fixing piece lose resilience due to the growth of human tissues, the two elastic claws can be forcibly pulled back to the initial state by rotating the locking roller, thus smoothly and quickly opening the sternum closing fixator.

9 Claims, 4 Drawing Sheets

(56) References Cited

U.S. PATENT DOCUMENTS

| | | | | |
|---|---|---|---|---|
| 2010/0198221 A1* | 8/2010 | Hearn | ................ | A61B 17/8009 |
| | | | | 606/71 |
| 2013/0338719 A1 | 12/2013 | Madjarov | | |
| 2015/0196396 A1* | 7/2015 | Thomas | ............. | A61B 17/8076 |
| | | | | 623/23.47 |
| 2021/0038276 A1* | 2/2021 | Schwagli | ............... | A61B 17/82 |

FOREIGN PATENT DOCUMENTS

| | | | |
|---|---|---|---|
| CN | 104107084 | A | 10/2014 |
| CN | 106108995 | A | 11/2016 |
| CN | 107961064 | A | 4/2018 |
| CN | 108941085 | A | 12/2018 |

\* cited by examiner

QUICK RELEASE STERNUM CLOSING FIXATOR

TECHNICAL FIELD

The present invention relates to the technical field of medical device, in particular to quick release sternum closing fixator.

BACKGROUND TECHNOLOGY

Thoracotomy requires the entire sternum to be dissected. At the end of the surgery, the traditional method of closing the sternum is to bundle up the entire sternum with steel wire from top to bottom, use a suture needle threaded by the steel wire to tighten the left and right dissected sternum with the steel wire, close the dissected sternum and then fix it. The traditional method of fixing the sternum with steel wire has the following disadvantages: 1. It is difficult to control and unify the tightness of fixing; 2. It's easy to cut the sternum with the steel wire, leading to sternal split and adverse consequences; 3. It is difficult to cross the steel wire.

On this basis, sternum closing fixator has gradually become favored by more and more doctors. At present, the sternum closing fixator has a male fixing piece and a female fixing piece, the outer side of the male fixing piece and the inner side of the female fixing piece are provided with matching serrations, the male fixing piece has a locking groove, and the locking groove is provided with a rotatable locking roller inside. By rotating the locking roller, the male fixing piece and the female fixing piece are locked with each other by the elastic deformation of the male fixing piece.

Chinese Patent CN103211632A discloses a sternum closing fixator, which comprises a locking roller, and a male fixing piece and a female fixing piece that can be plugged together, where the cross section of the locking roller is olive-shaped or oval; the male fixing piece has an elastic plug and the first claw hook plate, the elastic plug has the first serration on both sides and a tightening groove in the middle, the tightening groove is provided with a locking hole for transition fit with the outer wall surface of the locking roller, and the direction of long axis of the locking hole is the insertion direction of the male fixing piece and the female fixing piece; the female fixing piece has the second claw hook plate and a socket, the socket has a slot matched with the elastic plug, and the slot has the second serration matched with the first serration on both sides; the locking hole is installed with a rotatable locking roller inside, so that, by rotating the locking roller, the first serration can be engaged with the second serration when the tightening groove enlarges and the first serration can be separated from the second serration when the tightening groove becomes smaller. For this sternum closing fixator, since it requires a long time for the sternum to heal and some human tissues may grow on the male fixing piece and the female fixing piece, when it's necessary to have the second thoracotomy or remove the sternum closing fixator, the elastic claws of the male fixing piece will lose the resilience due to the growth of human tissues and thus can't smoothly and quickly open the sternum closing fixator after the locking roller rotates, which eventually makes it difficult to quickly and even rapidly remove the sternum closing fixator.

Chinese Patent CN104107084A discloses a claw-shaped sternum fixator, which comprises an inner claw hook plate and an outer claw hook plate, where the outer claw hook plate has a socket with a gear groove portion, the inner claw hook plate has a gear shaping portion matched with the gear groove portion, the inner claw hook plate is plugged together through the engagement of the gear spacing portion and the gear groove portion, the gear groove portion is provided with the first serration, the gear spacing portion is provided with the second serration matched with the first serration, the inner claw hook plate is further provided with a locking buckle and a locking hole matched with each other, and the locking buckle is hinged to the inner claw hook plate; when the locking buckle is rotated relative to the inner claw hook plate to fit into the locking hole, the said first serration of the gear groove portion and the second serration of the gear shaping portion will engage with each other so that the inner claw hook plate and the outer claw hook plate are tightly fitted. For this sternum closing fixator, since it requires a long time for the sternum to heal and some human tissues may grow on the male fixing piece and the female fixing piece, when it's necessary to have the second thoracotomy or remove the sternum closing fixator, the elastic claws of the male fixing piece will lose the resilience due to the growth of human tissues and thus can't smoothly and quickly open the sternum closing fixator after the locking buckle is opened, which eventually makes it difficult to quickly and even rapidly remove the sternum closing fixator.

Therefore, it is very necessary to improve the structure of the sternum closing fixator.

SUMMARY OF THE INVENTION

The technical problem to be solved by the present invention is that the elastic claws of the existing male fixing piece loses the resilience due to the growth of human tissues and thus can't smoothly and quickly open the sternum closing fixator. The present invention provides quick release sternum closing fixator, which has a tensioning device forcing the two elastic claws to move against each other between the said locking roller and the two elastic claws. After the locking roller rotates, when the elastic claws on the male fixing piece lose resilience due to the growth of human tissues, the two elastic claws can be forcibly pulled back to the initial state by rotating the locking roller, thus smoothly and quickly opening the sternum closing fixator. It is easy to operate and highly maneuverable.

The technical solution adopted by the present invention to solve the technical problem thereof is: quick release sternum closing fixator, which comprises a locking roller, and a male fixing piece and a female fixing piece that can be plugged together, Where the cross section of the locking roller is olive-shaped or oval, The male fixing piece has an elastic plug and the first claw hook plate, the elastic plug has the first serration on both sides and a tightening groove in the middle, thus forming two elastic claws, the tightening groove is provided with a locking hole for transition fit with the outer wall surface of the locking roller, and the direction of long axis of the locking hole is the insertion direction of the male fixing piece and the female fixing piece, The female fixing piece has the second claw hook plate and a socket, the socket has a slot matched with the elastic plug, and the slot has the second serration matched with the first serration on both sides, The locking hole is installed with a rotatable locking roller inside, so that, by rotating the locking roller, the two elastic claws can be distracted and the first serration can be engaged with the second serration when the direction of short axis of the locking roller is consistent with the insertion direction of the male fixing piece and the female fixing piece, and the first serration can be separated from the second serration when the direction of long axis of the locking roller is consistent with the insertion direction of the male fixing piece and the female fixing piece, A tensioning device forcing the two elastic claws to move against each other is provided between the said locking roller and the two elastic claws.

As a preferred embodiment, the said tensioning device comprises:

The upper flange formed on the upper surface of the locking roller, where two strain pins are formed on the upper flange surface, the strain pin and the locking roller are on the same side of the upper flange, and the two strain pins are symmetrically arranged on the two sides of the locking roller, The tensioning groove formed on the upper surface of the two elastic claws of the elastic plug, where the tensioning groove is in an arc shape on the side away from the locking hole and in a cut-off state on the side near the locking hole, and the said tensioning groove has a locking bulge on the side near the locking hole, The said strain pin is set in the tensioning groove, and when the direction of long axis of the locking roller is consistent with the insertion direction of the male fixing piece and the female fixing piece, the strain pin will fit with the locking bulge and tension the two elastic claws against each other.

As a preferred embodiment, the said locking bulge is located on the arc-shaped transitional surface with the side of the tensioning groove to facilitate the sliding of the strain pin, and the horizontal cross section of the locking bulge is wedge-shaped.

As a preferred embodiment, the said locking bulge has an arc-shaped positioning slot for fixing the strain pin on the side away from the tightening groove.

As a preferred embodiment, the included angle between the connecting line of the two strain pins and the long axis of the locking roller is 15°-90°.

As a preferred embodiment, the included angle between the connecting line of the two strain pins and the long axis of the locking roller is 30°-60°.

As a preferred embodiment, the said locking roller also has a lower flange and the locking roller is embedded in the locking hole through the upper flange and the lower flange.

As a preferred embodiment, an upper and lower stopper mechanism is provided between the said male fixing piece and the female fixing piece, The said upper and lower stopper mechanism comprises two fins and dovetail grooves matched with corresponding fins, the two fins are separately set on the two sides of the elastic plug and below the first serration, and the two dovetail grooves are separately set on the two sides of the slot on the socket and below the second serration.

As a preferred embodiment, the said locking roller has a rotation hole in the middle to facilitate the rotation of the locking roller.

As a preferred embodiment, the said slot is a straight slot running through the whole socket.

The advantages of the present invention are as follows: The present invention provides quick release sternum closing fixator, which has a tensioning device forcing the two elastic claws to move against each other between the said locking roller and the two elastic claws. After the locking roller rotates, when the elastic claws on the male fixing piece lose resilience due to the growth of human tissues, the two elastic claws can be forcibly pulled back to the initial state by rotating the locking roller, thus smoothly and quickly opening the sternum closing fixator. It is easy to operate and highly maneuverable. The locking bulge is located on the arc-shaped transitional surface with the side of the tensioning groove to facilitate the sliding of the strain pin, and the horizontal cross section of the locking bulge is wedge-shaped, so that when the locking roller rotates, the strain pin will not get stuck as touching the locking bulge for the first time on the arc-shaped transitional surface, thus smoothly tensioning the two elastic claws against each other.

BRIEF DESCRIPTION OF THE DRAWINGS

The present invention will be further described in the following in combination with the drawings and embodiments.

Figure 1:
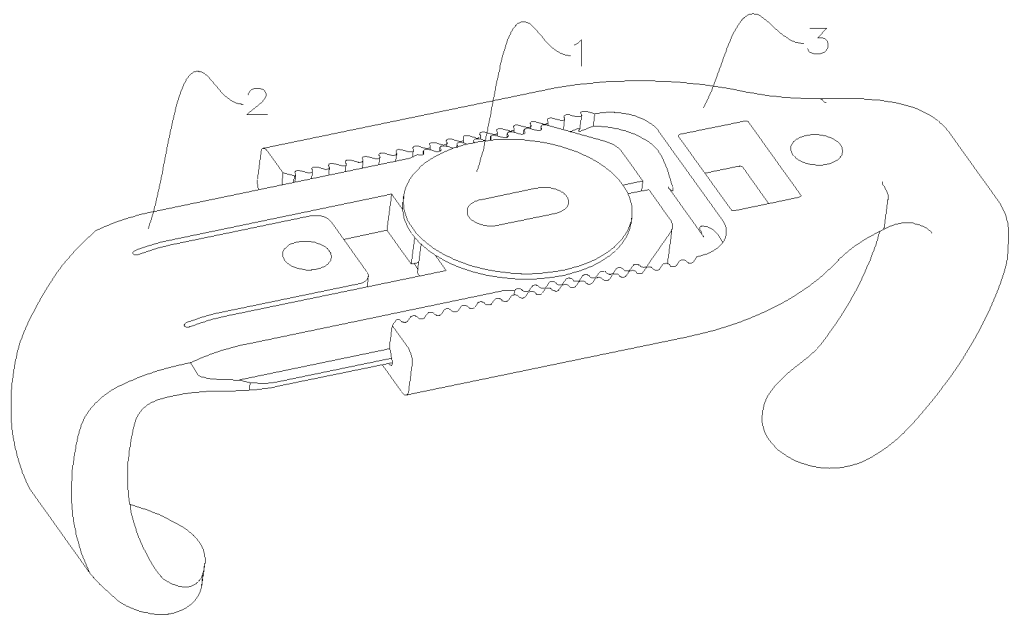
FIG. 1 is a structure diagram of quick release sternum closing fixator of the present invention.

In the figures: 1. locking roller, 2. male fixing piece, 3. female fixing piece, 4. arc-shaped transitional surface, 11. upper flange, 12. strain pin, 13. lower flange, 14. rotation hole, 21. elastic plug, 22. the first claw hook plate, 23. the first serration, 24. tightening groove, 25. elastic claw, 26. locking hole, 27. tensioning groove, 28. locking bulge, 29. positioning slot, 31. the second claw hook plate, 32. socket, 33. slot, 34. the second serration, 51. fin, 52. dovetail groove.

EMBODIMENTS

Now the present invention is further described in combination with the drawings. All these drawings are simplified schematic diagrams, which describe the basic structure of the present invention only in a schematic way. Therefore, only components related to the present invention are shown.

As shown in FIG. 1-FIG. 4, quick release sternum closing fixator, which comprises a locking roller 1, and a male fixing piece 2 and a female fixing piece 3 that can be plugged together, Where the cross section of the locking roller 1 is olive-shaped or oval, The male fixing piece 2 has an elastic plug 21 and the first claw hook plate 22, the elastic plug 21 has the first serration 23 on both sides and a tightening groove 24 in the middle, thus forming two elastic claws 25, the tightening groove 24 is provided with a locking hole 26 for transition fit with the outer wall surface of the locking roller 1, and the direction of long axis of the locking hole 26 is the insertion direction of the male fixing piece 2 and the female fixing piece 3, The female fixing piece 3 has the second claw hook plate 31 and a socket 32, the socket 32 has a slot 33 matched with the elastic plug 21, and the slot 33 has the second serration 34 matched with the first serration 23 on both sides, The locking hole 26 is installed with a rotatable locking roller 1 inside, so that, by rotating the locking roller 1, the two elastic claws 25 can be distracted and the first serration 23 can be engaged with the second serration 34 when the direction of short axis of the locking roller 1 is consistent with the insertion direction of the male fixing piece 2 and the female fixing piece 3, and the first serration 23 can be separated from the second serration 34 when the direction of long axis of the locking roller 1 is consistent with the insertion direction of the male fixing piece 2 and the female fixing piece 3, A tensioning device forcing the two elastic claws 25 to move against each other is provided between the said locking roller 1 and the two elastic claws 25.

Figure 2:
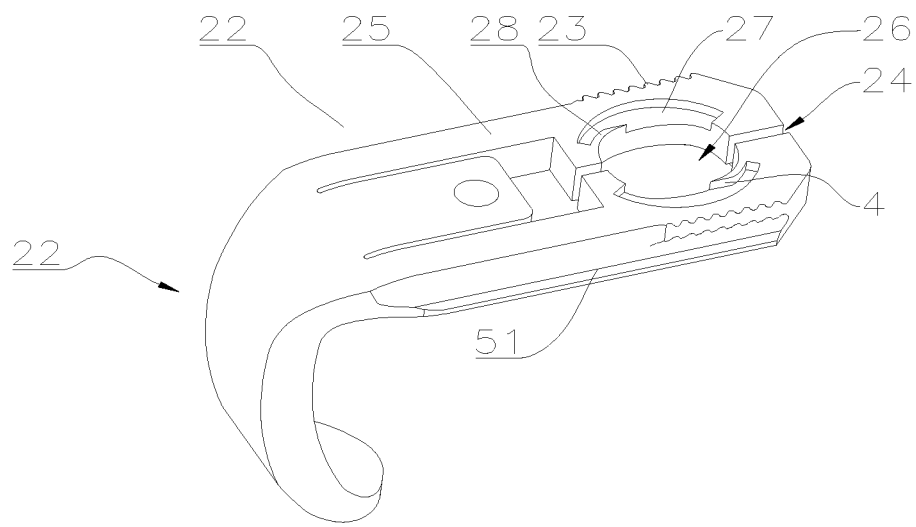
FIG. 2 is a perspective view of the male fixing piece of the present invention.
Figure 3:
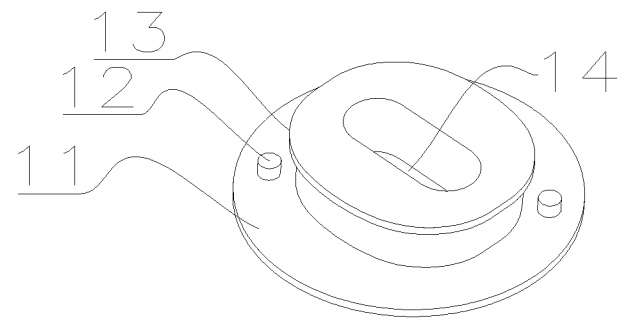
FIG. 3 is a perspective view of the locking roller of the present invention.
Figure 4:
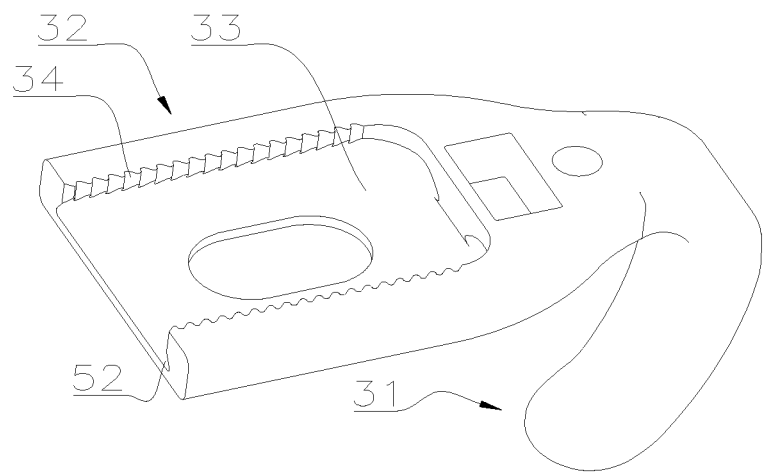
FIG. 4 is a perspective view of the female fixing piece of the present invention.

In one embodiment as shown in FIG. 2-FIG. 4, the tensioning device comprises:

The upper flange 1 formed on the upper surface of the locking roller 1, where two strain pins 12 are formed on the upper flange 11 surface, the strain pin 12 and the locking roller 1 are on the same side of the upper flange 11, and the two strain pins 12 are symmetrically arranged on the two sides of the locking roller 1, The tensioning groove 27 formed on the upper surface of the two elastic claws 25 of the elastic plug 21, where the tensioning groove 27 is in an arc shape on the side away from the locking hole 26 and in a cut-off state on the side near the locking hole 26, and the said tensioning groove 27 has a locking bulge 28 on the side near the locking hole 26, The said strain pin 12 is set in the tensioning groove 27, and when the direction of long axis of the locking roller 1 is consistent with the insertion direction of the male fixing piece 2 and the female fixing piece 3, the strain pin 12 will fit with the locking bulge 28 and tension the two elastic claws 25 against each other. Because the tensioning groove 27 is in a cut-off state on the side near the locking hole 26, it is easy to install the locking roller 1. During the installation, the strain pin 12 enters the tensioning groove 27 through the side near the locking hole 26 where the tensioning groove 27 is in a cut-off state.

In one embodiment as shown in FIG. 3, the locking bulge 28 is located on the arc-shaped transitional surface 4 with the side of the tensioning groove 27 to facilitate the sliding of the strain pin 12, and the horizontal cross section of the locking bulge 28 is wedge-shaped. When the locking roller 1 rotates, the strain pin 12 will not get stuck as touching the locking bulge 28 for the first time on the arc-shaped transitional surface 4, thus smoothly tensioning the two elastic claws 25 against each other.

Figure 7:
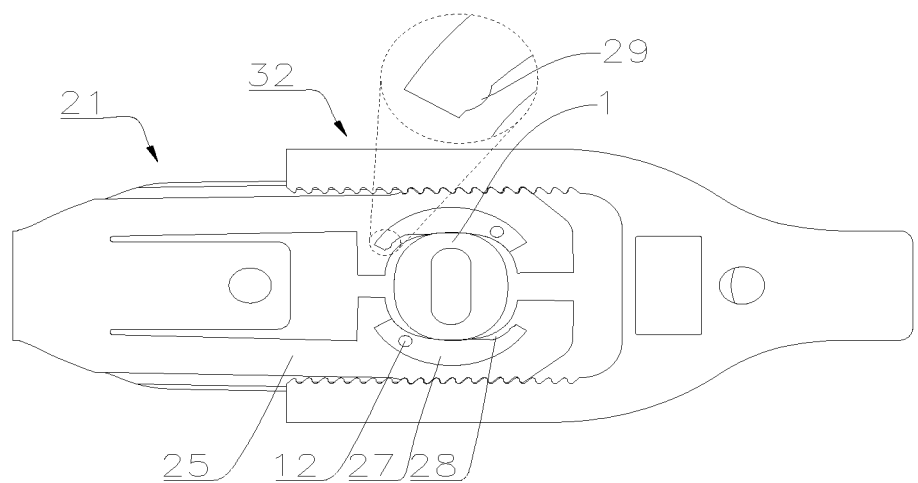
FIG. 7 is a structure diagram of the sternum closing fixator with the positioning slot of the present invention, with the upper flange omitted.

In one embodiment as shown in FIG. 7, the locking bulge 28 has an arc-shaped positioning slot 29 for fixing the strain pin 12 on the side away from the tightening groove 24. When the two elastic claws 25 are tensioned against each other, the rotation of locking roller 1 will be stopped. Now the strain pin 12 is stuck in the positioning slot 29, which maintains the elastic claws 25 in a tensioning state. The configuration of the arc-shaped positioning slot 29 enables the elastic claws 25 to maintain a tensioning state without affecting the rotation of the locking roller 1.

In one embodiment, the included angle between the connecting line of the two strain pins 12 and the long axis of the locking roller 1 is 15°-90°. In this embodiment, the included angle between the connecting line of the two strain pins 12 and the long axis of the locking roller 1 is preferred to be 30°-60°.

In one embodiment as shown in FIG. 3, the locking roller 1 also has a lower flange 13 and the locking roller 1 is embedded in the locking hole 26 through the upper flange 11 and the lower flange 13.

In one embodiment, an upper and lower stopper mechanism is provided between the said male fixing piece 2 and the female fixing piece 3. The upper and lower stopper mechanism comprises two fins 51 and dovetail grooves 52 matched with corresponding fins 51, the two fins 51 are separately set on the two sides of the elastic plug 21 and below the first serration 23, and the two dovetail grooves 52 are separately set on the two sides of the slot 33 on the socket 32 and below the second serration 34.

In one embodiment, the locking roller 1 has a rotation hole 14 in the middle to facilitate the rotation of the locking roller 1.

In one embodiment, the slot 33 is a straight slot running through the whole socket 32.

Figure 5:
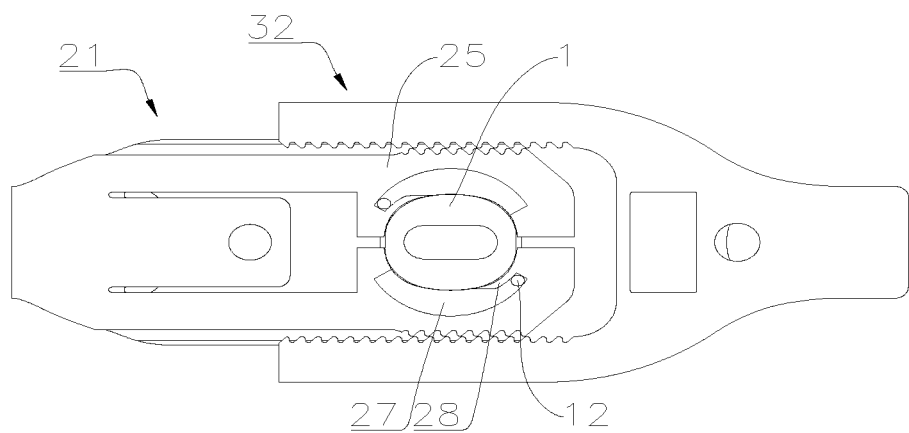
FIG. 5 is a schematic diagram of the tensioning structure of the sternum closing fixator of the present invention, with the upper flange omitted.
Figure 6:
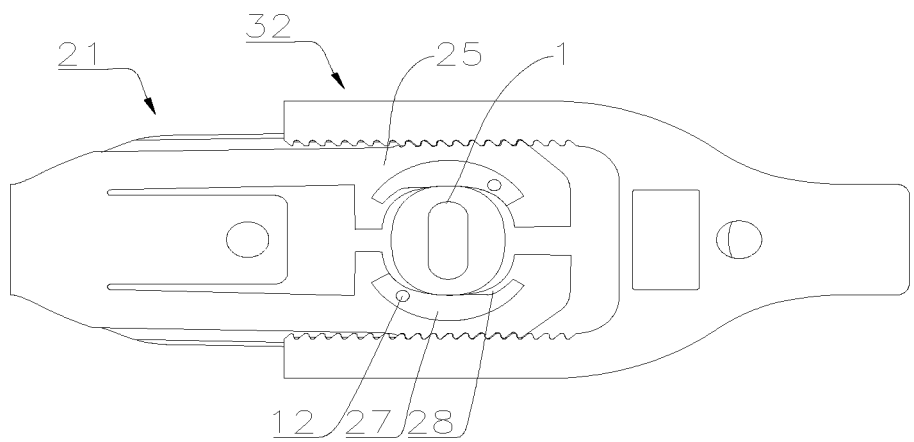
FIG. 6 is a schematic diagram of the locking structure of the sternum closing fixator of the present invention, with the upper flange omitted.

When using the quick release sternum closing fixator of this application, first make the male fixing piece 2 and the female fixing piece 3 in a state as shown in FIG. 5, adjust the distance between the male fixing piece 2 and the female fixing piece 3 to a suitable extent, and rotate the locking roller 1 that is olive-shaped or oval. During the rotation, gradually distract the two elastic claws 25, to make the first serration 23 engage with the second serration 34. When the direction of short axis of the locking roller 1 is consistent with the insertion direction of the male fixing piece 2 and the female fixing piece 3, the locking roller 1 has rotated to the limiting position and the fixation of the sternum closing fixator is completed, as shown in FIG. 6. When it's necessary to have the second thoracotomy or remove the sternum closing fixator, rotate the locking roller 1. The locking roller 1 drives the strain pin 12 to rotate in the tensioning groove 27, making the strain pin 12 touch the locking bulge 28. Pulled by the locking bulge 28, the two elastic claw 25 are tensioned against each other, forcing the first serration 23 to separate from the second serration 34. When the direction of long axis of the locking roller 1 is consistent with the insertion direction of the male fixing piece 2 and the female fixing piece 3, the locking roller 1 has rotated to the limiting position and the first serration 23 and the second serration 34 are totally separated, as shown in FIG. 5.

Inspired by the above ideal embodiments based on the present invention and through the above specification, various changes and modifications may be made by those skilled in the art without deviating from the technical scope of the present invention. The technical scope of the present invention is not limited to the contents in the specification but must be determined according to the scope of claims.

The invention claimed is:
1. A quick release sternum closing fixator, comprising:
a locking roller, and a male fixing piece and a female fixing piece configured to engage each other,
wherein a cross section of the locking roller is olive-shaped or oval in shape,
wherein the male fixing piece has an elastic plug and a first claw hook plate, the elastic plug has a first serration on each of two side surfaces and a tightening groove disposed in the middle, thus forming two elastic claws, the tightening groove is provided with a locking hole for a transition fit with an outer wall surface of the locking roller, and the direction of a long axis of the locking hole is the aligned with the direction in which the male fixing piece engages the female fixing piece, wherein the female fixing piece has a second claw hook plate and a socket, the socket has a slot matching the elastic plug, and the slot has a second serration matching the first serration on both sides each of the two side surfaces, wherein the locking hole is installed with the locking roller inside so that, by rotating the locking roller, the two elastic claws are distracted and the first serration engages the second serration when the direction of a short axis of the locking roller aligned with the direction in which the male fixing piece engages the female fixing piece, and the first serration is separable from the second serration when the direction of long axis of the locking roller is aligned with the direction in which the male fixing piece and engages the female fixing piece, wherein a tensioning device forcing the two elastic claws to move against each other is provided between the locking roller and the two elastic claws, wherein the tensioning device comprises:

an upper flange formed on an upper surface of the locking roller, wherein the two strain pins are symmetrically arranged on the upper flange, a tensioning groove is formed on the upper surface of each of the two elastic claws of the elastic plug, wherein the tensioning groove is in an arc shape on the side away from the locking hole and in a cut-off state on the side near the locking hole, and the tensioning groove has a locking bulge on the side near the locking hole, and wherein each of the two strain pins is set in the respective tensioning groove, and when the direction of the long axis of the locking roller is aligned with the direction in which the male fixing piece engages the female fixing piece, the strain pin fits with the locking bulge and tensions the two elastic claws against each other.

2. The quick release sternum closing fixator according to claim 1, wherein the locking bulges are each located on arc-shaped transitional surface with the side of the tensioning groove to facilitate sliding of the strain pin, and the horizontal cross section of the locking bulge is wedge-shaped.

3. The quick release sternum closing fixator according to claim 1, wherein the locking bulges each has an arc-shaped positioning slot for fixing the strain pin on the side away from the tightening groove.

4. The quick release sternum closing fixator according to claim 1, wherein the included angle between the connecting line of the two strain pins and the long axis of the locking roller is 15°-90°.

5. The quick release sternum closing fixator according to claim 4, wherein the included angle between the connecting line of the two strain pins and the long axis of the locking roller is 30°-60°.

6. The quick release sternum closing fixator according to claim 1, wherein the locking roller also has a lower flange and the locking roller is embedded in the locking hole through the upper flange and the lower flange.

7. The quick release sternum closing fixator according to claim 1, wherein an upper and lower stopper mechanism is provided between the male fixing piece and the female fixing piece, the upper and lower stopper mechanism comprises two fins and dovetail grooves matching corresponding fins, the two fins are separately set on the two sides of the elastic plug and below the first serration, and the two dovetail grooves are separately set on the two sides of the slot on the socket and below the second serration.

8. The quick release sternum closing fixator according to claim 1, wherein the locking roller has a rotation hole in the middle to facilitate the rotation of the locking roller.

9. The quick release sternum closing fixator according to claim 1, wherein the slot is a straight slot running through the whole socket.

\* \* \* \* \*